United States Patent
Haldar et al.

(10) Patent No.: US 7,534,381 B2
(45) Date of Patent: May 19, 2009

(54) PROCESS AND APPARATUS FOR FORMING AGGLOMERATES OF A POWDER COMPOSITION OF AN ACTIVE AND BINDER

(75) Inventors: Rama Haldar, Randolph, NJ (US); Dipan B. Ray, Old Bridge, NJ (US); William Drefko, Kearny, NJ (US); Sidney Etienne, Ridgefield Park, NJ (US)

(73) Assignee: ISP Investments Inc., Wilmington, DE (US)

( * ) Notice: Subject to any disclaimer, the term of this patent is extended or adjusted under 35 U.S.C. 154(b) by 441 days.

(21) Appl. No.: 11/226,574

(22) Filed: Sep. 14, 2005

(65) Prior Publication Data

US 2007/0060494 A1 Mar. 15, 2007

(51) Int. Cl.
*B29C 43/02* (2006.01)
(52) U.S. Cl. .................. 264/120; 264/109
(58) Field of Classification Search .......... None
See application file for complete search history.

(56) References Cited

U.S. PATENT DOCUMENTS

| | | | | | |
|---|---|---|---|---|---|
| 4,801,460 | A | * | 1/1989 | Goertz et al. | 514/772.5 |
| 5,073,379 | A | * | 12/1991 | Klimesch et al. | 424/467 |
| 2003/0220460 | A1 | * | 11/2003 | Merfeld | 526/347.2 |
| 2004/0138263 | A1 | * | 7/2004 | D'Angio et al. | 514/323 |
| 2004/0235850 | A1 | * | 11/2004 | Waterman | 514/249 |
| 2005/0084560 | A1 | * | 4/2005 | Roland | 425/363 |
| 2005/0118542 | A1 | * | 6/2005 | Mori et al. | 430/619 |
| 2005/0202088 | A1 | * | 9/2005 | Hanshermann et al. | 424/471 |

FOREIGN PATENT DOCUMENTS

WO WO 03/101428 * 12/2003

* cited by examiner

*Primary Examiner*—Mary Lynn F Theisen
(74) *Attorney, Agent, or Firm*—William J. Davis

(57) ABSTRACT

A process and apparatus for forming agglomerates of a powder composition of an active and binder such as a homopolymer or copolymer which includes passing the composition through a hot roller compactor to heat said binder material above its glass transition temperature.

17 Claims, 1 Drawing Sheet

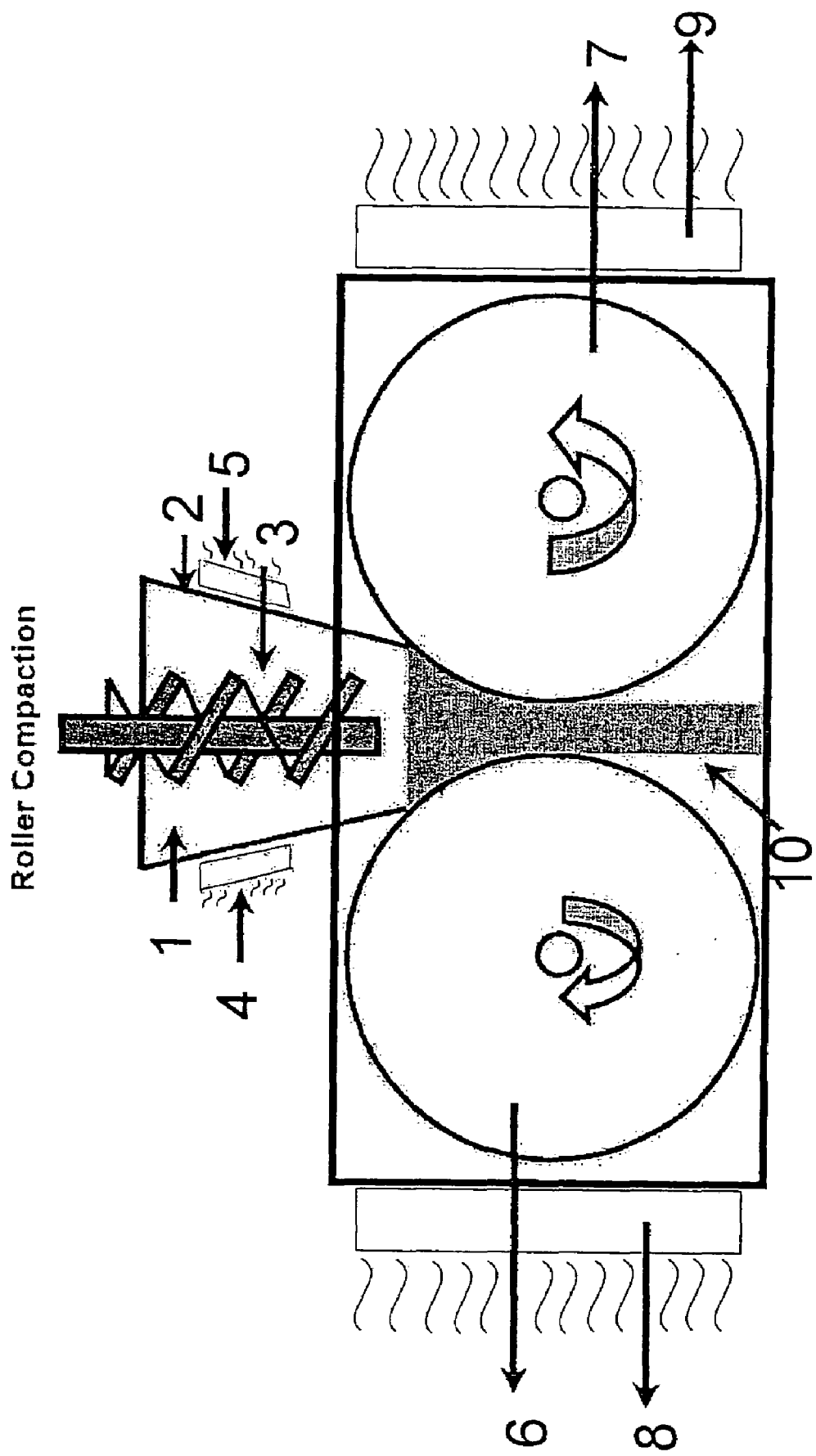

PROCESS AND APPARATUS FOR FORMING AGGLOMERATES OF A POWDER COMPOSITION OF AN ACTIVE AND BINDER

BACKGROUND OF THE INVENTION

1. Field of the Invention

This invention relates to a process and apparatus for forming agglomerates of an active and binder, and more particularly, to making such agglomerates by hot roller compaction.

2. Description of the Prior Art

There is a great need particularly in the pharmaceutical industry for an alternative and cost effective process to wet granulation for preparing granules of an active from which tablets and/or capsules can be made, particularly for moisture sensitive drug actives. Wet granulation using alcohol or other volatile solvents is disadvantageous because it requires solvent recovery.

R. Klimesch et al in U.S. Pat. No. 5,073,379 and H. Goertz et al in U.S. Pat. No. 4,801,460 describes the preparation of solid pharmaceutical forms by injection molding or extrusion.

Accordingly, it is an object of this invention to provide a method and apparatus for preparation of granules of an active by hot roller compaction.

Another object of the invention is to provide such a process and apparatus which does not require solvents, is a one-step process and is also suitable for moisture sensitive drugs.

Still another object herein is to provide such a process and apparatus which produces granules that can be compressed into tablets; having excellent dissolution properties.

These and other objects and features of the invention will be made apparent from the following description.

SUMMARY OF THE INVENTION

What is described herein is a process and apparatus for forming agglomerates of a powder composition of an active and binder by passing the composition through a hot roller compactor to heat the binder ingredient in situ to a temperature above its glass transition temperature.

The process herein also includes the steps of milling the agglomerates into granules, and thereafter forming tablets or filled into capsules.

The apparatus of the invention includes a roller compactor through which the composition is passed, and heating means associated with said compactor to heat the binder above its glass transition temperature.

Suitably the heating means is provided by hot oil within the rollers, or external electric, steam or hot air heating means.

Suitable binder ingredients include polymers, such as homopolymer or copolymers of vinyl pyrrolidone, and cellulosic polymers.

Suitable actives include pharmaceutical, nutritional, and cosmetic materials, particularly poorly compressible and/or moisture sensitive actives.

IN THE DRAWING

The FIGURE is a schematic representation of suitable apparatus for forming agglomerates of an active and binder useful in the process of the present invention.

DETAILED DESCRIPTION OF THE INVENTION

Roll compaction is a dry compaction-granulation process in which uniformly mixed powders are compressed between two counterrotating roll pairs to form a compressed sheet or ribbon that is then milled (granulated). The advantages of roll compaction technology in the pharmaceutical industry include a dry granulation system, high-volume production of granules, and good control of final particle bulk density and flow properties.

The roller compactor is a densification and dry granulation machine that produces uniform compacted sheets with consistent hardness and increased density by compacting powdered material between two uniquely designed rolls.

The roller compactor utilizes a cantilevered roll design and features a vertical combination tapered-to-straight feed screw system and the compaction rolls. A uniform compaction force is distributed to the rolls due to consistent product feeding to and across the face of the compaction rolls.

A combination tapered-to-straight screw feeder inside the hopper precompacts and deaerates the powder for optimum product feeding. The screw feeder delivers deaerated powder into the roll nip area and seal system. The roll seal system consists of top and side seals to confine the powder to the roll nip area, and to minimize leakage of uncompacted powder.

A roller compactor is available commercially as the TFC-Roller Compactor sold by the Vector Corporation.

Referring now to the FIGURE, there is shown the hot roller compaction, apparatus of the invention useful in forming agglomerates of an active and binder composition according to the process of the present invention.

The apparatus includes a hopper 2 containing composition 1 in which is located screw feed auger 3. Heater elements 4 and 5 are positioned outside the hopper to preheat the composition before it passes through rollers 6 and 7. The rollers are heated by elements 8 and 9 to heat composition 1 above its glass transition temperature. After exiting the rollers the composition exits as an in-situ formed agglomerate 10.

Suitable binder ingredients include polymers such as a homopolymer or copolymer of vinyl pyrrolidone, e.g. Plasdone® S-630 (ISP), and plasticized polymers thereof and mixtures of such binder ingredients.

Suitably the binder ingredient is present in an amount of about 1 to 20% by weight of the composition, preferably 5-15%.

Actives such as described in U.S. Pat. No. 5,073,379, col. 5-6 are typical pharmaceuticals.

EXAMPLE 1

The drug acetaminophen in powder form was granulated in a composition of Table 1 with 10% by wt. of plasticizer copolymer of polyvinylpyrrolidone-vinyl acetate copolymer (ISP) (Plasdone SDC) (90:10) by the hot roller compaction apparatus of the FIGURE. The rolls were heated to 95° C. using two ceramic heaters positioned about 1½" away from the rolls. The roll speed was 4 rpm, the screw speed was 12 rpm and the compaction pressure was 2500 psi. The resultant product were ribbons of agglomerated material. The collected material then was passed through an 18 mesh screen to produce granules of the composition.

TABLE 1

| Ingredient | Wt. % |
| --- | --- |
| Acetaminophen | 87.3 |
| Plasdone SDC (ISP) | 9.7 |
| Polyplasdone ® XL (ISP) | 2.0 |
| Magnesium stearate | 0.5 |
| Cabosil ® (Cabot) (silica) | 0.5 |
| | 100.0% |

After hot roller compaction and screening of the composition above, the granules were compressed into tablets.

What is claimed is:

1. A process of forming agglomerates of an active and a binder comprising:
   providing a powder composition comprising an active and a binder at a temperature below the glass transition temperature of the binder;
   precompacting and deaerating the powder composition; and
   passing said powder composition through a hot roller compactor to heat the binder to a temperature above its glass transition temperature thereby forming agglomerates of the composition.

2. A process according to claim 1 which also includes the steps of milling said agglomerates into granules, and thereafter compressing the granules into tablets or filling the granules into capsules.

3. A process according to claim 1 wherein said active is a pharmaceutical, nutritional or cosmetic material.

4. A process according to claim 3 wherein said active is a poorly compressible or moisture sensitive active.

5. A process according to claim 1 wherein said polymer is a copolymer of vinyl pyrrolidone or a plasticized copolymer of vinyl pyrrolidone.

6. A process according to claim 1 wherein said binder is present in an amount of about 1% to 20% by weight of the composition.

7. A process according to claim 6 wherein said binder is present in an amount of about 5% to 15% by weight of the composition.

8. A process according to claim 1 wherein the binder is selected from the group consisting of homopolymers of vinyl pyrrolidone, copolymers of vinyl pyrrolidone, plasticized polymers thereof, and mixtures thereof.

9. A process of forming agglomerates of an active and a binder comprising:
   providing a powder composition comprising an active and a binder at a temperature below the glass transition temperature of the binder;
   preheating the powder composition; and
   passing said powder composition through a hot roller compactor to heat the binder to a temperature above its glass transition temperature thereby forming agglomerates of the composition.

10. A process according to claim 9 further comprising milling said agglomerates into granules.

11. A process according to claim 9 further comprising precompacting and deaerating the powder composition before passing the composition through the hot roller compactor.

12. A process according to claim 9 wherein said binder comprises a copolymer of vinyl pyrrolidone or a plasticized copolymer of vinyl pyrrolidone.

13. A process according to claim 9 wherein said binder is present in an amount of about 1% to 20% by weight of the composition.

14. A process according to claim 13 wherein the binder is present in an amount of about 5% to 15% by weight of the composition.

15. A process according to claim 14 wherein said binder comprises a copolymer of vinyl pyrrolidone or a plasticized copolymer of vinyl pyrrolidone.

16. A process according to claim 9 wherein the binder is selected from the group consisting of homopolymers of vinyl pyrrolidone, copolymers of vinyl pyrrolidone, plasticized polymers thereof, and mixtures thereof.

17. A process according to claim 9 wherein the active is a pharmaceutical, nutritional or cosmetic material.

\* \* \* \* \*